United States Patent
Schwarz et al.

(10) Patent No.: US 6,423,858 B1
(45) Date of Patent: Jul. 23, 2002

(54) MANUFACTURING PROCESS FOR AMINOALKYL SILANES

(75) Inventors: Christoph Schwarz, Marl; Frank Kropfgans; Hartwig Rauleder, both of Rheinfelden; Hermann-Josef Korte, Haltern, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/991,965

(22) Filed: Nov. 26, 2001

(30) Foreign Application Priority Data

Nov. 25, 2000 (DE) .......................... 100 58 620

(51) Int. Cl.$^7$ ................................. C07F 7/10
(52) U.S. Cl. ........................................ 556/413
(58) Field of Search ........................... 532/413

(56) References Cited

U.S. PATENT DOCUMENTS

| | | | | |
|---|---|---|---|---|
| 4,234,502 A | * | 11/1980 | Kappler et al. | 556/413 |
| 4,234,503 A | * | 11/1980 | Kappler et al. | 556/413 |
| 5,616,755 A | * | 4/1997 | Seiler et al. | 556/413 |
| 5,698,726 A | * | 12/1997 | Rauleder et al. | 556/413 |
| 5,808,123 A | * | 9/1998 | Balduf et al. | 556/413 |
| 6,310,230 B1 | * | 10/2001 | Koski | 556/413 |

\* cited by examiner

Primary Examiner—Paul F. Shaver
(74) Attorney, Agent, or Firm—Oblon, Spivak, McClelland, Maier & Neustadt, P.C.

(57) ABSTRACT

Aminoalkylsilanes of formula I:

$$R^1R^2N-(CH_2)_y-Si(OR^3)_{3-n}R^4{}_n \qquad (I),$$

wherein $R^1$ and $R^2$ are each independently, identical of different, hydrogen, aryl, arylalkyl or $C_{1-4}$-alkyl; $R^3$ and $R^4$ are each independently, identical or different, $C_{1-8}$-alkyl or aryl; y is 2, 3 or 4 and n is 0 or 1, 2 or 3, are prepared by a process comprising:

reacting an organosilane of formula II:

$$X-(CH_2)_y-Si(OR^3)_{3-n}R^4{}_n \qquad (II),$$

wherein X is Cl, Br, I or F; and $R^3$, $R^4$, y and n are each as defined above with ammonia or an organic amine compound of the formula:

$$HNR^1R^2 \qquad (III),$$

wherein $R^1$ and $R^2$ are each as defined above with at least one of $R^1$ and $R^2$ not being hydrogen in a liquid phase;

evaporating ammonia or organic amine under reduced pressure while ammonium chloride or aminohydrochloride by-products, produced in the reaction of the first step, remains dissolved in the liquid phase;

transferring the product mixture after said evaporation to another vessel operated at a lower pressure level of than the second stage, and allowing ammonium chloride or aminohydrochloride to crystallize;

separating the crystalline ammonium chloride or aminohydrochloride from the crude product; and distilling the crude product to produce purified aminoalkylsilane product.

12 Claims, No Drawings

MANUFACTURING PROCESS FOR AMINOALKYL SILANES

BACKGROUND OF THE INVENTION

1. Field of the Invention

The present invention relates to a process for manufacturing aminoalkylsilanes.

2. Description of the Background

A method for manufacturing aminoalkylsilanes, of which 3-aminopropyltriethoxysilane (AMEO) is an example, is known, wherein a chloroalkylsilane, such as 3-chloropropyltriethoxysilane (CPTEO), reacts in batches with an excess of ammonia or an organic amine in liquid phase, for example, with ammonia at T=90° C., p=50 bar abs. and time=6 h. The product is then evaporated or concentrated and the pressure is reduced, at which point excess ammonia escapes and ammonium chloride is yielded in crystalline form. The evaporation process generally requires a period of time of over 10 hours. The ammonium chloride is usually separated from the crude product by filtration. The crude product is then distilled (DE-OS 27 49 316, DE-OS 27 53 124). However, a distinct disadvantage of this process is that, when the pressure is reduced over the product mixture, instances of caking occur, involving cakes of ammonium chloride or aminohydrochlorides. These cakes appear on the wall of the synthesis reactor, as well as on the stirring apparatus, and have a negative influence on heat transfer during the evaporation process. The deposits and caking require the plant to be at a frequent standstill, in which case the synthesis reactor has to be shut down, emptied, opened, filled with water in order to dissolve the ammonium salt crust, or freed of the cakes by mechanical means, then dried and closed.

EP 0 849 271 A2 also discloses the manufacture of 3-aminopropyltrialkoxysilanes from 3-chloropropyltrialkoxysilanes and ammonia by continuous operation. However, the disadvantage of this process is that even with a 100 fold excess of ammonia in relation to chloropropyltrialkoxysilane and an additional secondary reaction at 120° C., a 95% maximum yield of crude silane mixture is only obtained from primary, secondary and tertiary aminosilanes.

Apart from the distillation and separation of precipitated ammonium chloride, additional pressure extraction is required for product separation. A need, therefore, continues to exist for an improved process of manufacturing 3-aminopropylalkoxysilanes.

SUMMARY OF THE INVENTION

Accordingly, one object of the invention is to provide an improved and more efficient process for manufacturing amninoalkylsilanes, particularly for the manufacture of 3-aminopropylalkoxysilanes.

Briefly, this object and other objects of the present invention as hereinafter will become more readily apparent can be attained by a process for the manufacture of aminoalkylsilanes of formula I:

$$R^1R^2N-(CH_2)_y-Si(OR^3)_{3-n}R^4_n \qquad (I)$$

wherein $R^2$ and $R^2$ are each independently, identical of different, hydrogen, aryl, arylalkyl or $C_{1-4}$-alkyl; $R^3$ and $R^4$ are each independently, identical or different, $C_{1-8}$-alkyl or aryl; y is 2, 3 or 4 and n is 0 or 1, 2 or 3, comprising:

reacting an organosilane of formula II:

$$X-(CH_2)_y-Si(OR^3)_{3-n}R^4_n \qquad (II),$$

wherein X is Cl, Br, I or F; and $R^3$, $R^4$, y and n are each as defined above with ammonia or an organic amine compound of the formula:

$$HNR^1R^2 \qquad (III),$$

wherein $R^1$ and $R^2$ are each as defined above with at least one of $R^1$ and $R^2$ not being hydrogen in a liquid phase;

evaporating ammonia or organic amine under reduced pressure while ammonium chloride or aminohydrochloride by-products, produced in the reaction of the first step, remains dissolved in the liquid phase;

transferring the product mixture after said evaporation to another vessel operated at a lower pressure level of than the second stage, and allowing ammonium chloride or aminohydrochloride to crystallize;

separating the crystalline ammonium chloride or aminohydrochloride from the crude product; and distilling the crude product to produce purified aminoalkylsilane product.

DETAILED DESCRIPTION OF THE PREFERRED EMBODIMENTS

It has now been discovered, surprisingly, that aminoalkylsilanes can be manufactured simply and economically by reacting an alkylarylsilane, such as 3-chloropropyltriethoxy silane (CPTEO), in a first process stage with an excess of ammonia or an organic amine used in excess in a liquid phase, and then evaporating ammonia or organic amine in a second process stage under reduced pressure, wherein a substantial portion of excess ammonia or organic amine escapes and ammonium chloride or predominantly aminohydrochloride remains, appropriately fully dissolved in a liquid phase. The product mixture from the second process stage is then transferred to a vessel, operated at a lower level of pressure than in the evaporation step, and ammonium chloride or aminohydrochloride crystallizes. The crystalline ammonium chloride or aminohydrochloride is separated from the crude product and finally the crude product is processed by distillation to provide purified aminoalkylsilane product.

The present invention, in particular, provides an effective method of producing aminoalkylsilanes having formula I above by the reaction of an organosilane having formula II shown above with ammonia or a nitrogen compound having formula III shown above.

Preferred suitable 3-chloralkylalkoxysilanes include 3-chloropropyltriethoxysilane, 3-chloropropyltrimethoxysilane, 3-chloropropylmethyldimethoxysilane and 3-chloropropylmethyldiethoxysilane as the organosilane of formula II. However, other chloralkylalkoxysilanes, such as, for example, 3-chloropropyldiethylmethoxysilane or 3-chloropropylethylpropylethoxysilane, can also be employed in the present process.

In the process of the present invention ammonia, methylamine, ethylamine or diethylamine is preferably used as nitrogen containing constituent having formula III.

Examples of products of the present invention which can be manufactured simply and economically include 3-aminopropyltriethoxysilane, 3-aminopropyltrimethoxysilane, 3-aminopropylmethyldiethoxysilane and N-methyl-3-aminopropyltrimethoxysilane, to name but a few.

In the process of the present invention organosilanes of formula II and ammonia or an organic amine of formula III in liquid form are usually fed to a pressure reactor, in which case it is suitable to set the molar ratio of chloralkylalkoxysilane to ammonia or organic amine compound at 1:10 to 1:50. In the first process stage conversion generally takes place at a pressure of 25 to <100 bar abs. and at a temperature of 50 to <110° C., wherein conversion is almost complete. In addition, the almost complete portion of ammonium chloride or aminohydrochloride by-product remains dissolved in the liquid phase. Preferably more than 99%, in particular preferably 99.9% to 100%, of the ammonium chloride or aminohydrochloride resulting from the reaction remains dissolved in the liquid phase of the first stage. The resulting product mixture is then transferred to the second process stage, in which case the second process stage is performed at a substantially lower pressure than the first process stage. In the process, considerable quantities of ammonia are flashed removed, for example, 50% to 80% by weight of the excess ammonia or organic amine. This removal of excess reactant is effected by using an operating procedure in which the pressure transitions from 50 to 15 to 20 bar abs.

The second evaporative stage is normally performed at pressures of >10 to <50 bar abs., preferably 11 to 35 bar abs., more preferably 13 to 25 bar abs., and most preferably 15 to 20 bar abs., and at a temperature of >10 to <110° C., preferably 20° C. to 95° C., more preferably 30° C. to 85° C., and most preferably 35° C. to 80° C., so that ammonium chloride or aminohydrochloride remains almost completely dissolved in a liquid phase This procedure enables problems which arise from the accumulation of solids to be prevented as desired. In general, the evaporation times result from the excess quantities of ammonia and amine of the reaction and the available evaporation apparatus, evaporator surfaces and the like as well as the structure of the plant being used. With the process of the present invention there is a large degree of freedom for selecting appropriate and cost-effective plant components for the above-mentioned evaporation processes because of the practically solids-free operation in the second evaporative stage. The product dwell time in the second evaporative stage ranges from 0.1 to 4 hours, preferably from 0.1 to 2 hours, in particular from 0.1 to 1 hour.

After the evaporation step, the crystallization of the ammonium chloride or aminohydrochloride by-product occurs in a the third step, which is conducted, for example, in a crystallizer equipped with an agitator. Crystallization is generally conducted at a pressure below the final pressure of the second evaporative stage, preferably at 1 to 6 bar abs., wherein the solubility limits of ammonium chloride or amine hydrochloride are not reached. These by-products are obtained particularly gently in crystalline form. The operating temperature of the crystallization stage is as a rule in the range of 20° C. to 60° C. The solids can be separated from the product in a know manner and then the crude product processed by distillation.

The process according to the present invention is generally carried out as follows: In a first process stage an organosilane of general formula II is caused to react with excess ammonia or organic amine in a liquid phase and the resulting product mixture is transferred to the second process stage, where ammonia or organic amine is evaporated under reduced pressure and resulting ammonium chloride or aminohydrochloride remains dissolved in the liquid phase. The product mixture from the second process stage is then transferred to a third process stage, operated at a lower level of pressure than the second stage, and ammonium chloride or aminohydrochloride is crystallized out and separated from the crude product. The mixture can be separated by filtering. The resulting crude aminoalkylsilane product can be processed by distillation.

The process of the present invention is distinguished by the following advantages:

The batch time in the present process can be at least halved, compared to that disclosed in DE-PS 27 49 316 or DE-OS 27 53 124, resulting in a doubling of the plant capacity.

Caking usually no longer appears in the synthesis reactors.

Almost no solids accumulate in the second evaporative step, which allows power to be introduced to the process at a favorable point to evaporate the majority of ammonia or organic amine.

The pressure graduation of the process stages of the present invention allows the use of more cost-effective apparatus for broad processing areas in process stages 2 or 3, in comparison to the respective preceding process steps.

Smaller apparatus can also be utilized in subsequent steps because of the reduced quantities of ammonia or organic amine, as compared to the preliminary step.

Having now generally described this invention, a further understanding can be obtained by reference to certain specific examples which are provided herein for purposes of illustration only and are not intended to be limiting unless otherwise specified.

EXAMPLES

Example 1

Manufacture of 3-aminopropyltriethoxy silane

In an autoclave fitted with an agitator 7.5 kg (31.1 mol) 3-chloropropyltriethoxysilane are reacted with 24 kg (1412 mol) ammonia at 48 to 50 bar and approximately 100° C. within 6 hours. After this period 3-chloropropyltriethoxy silane is detectable in the 3-aminopropyltriethoxysilane crude product which is formed by means of GC analysis in trace amounts only. The ammonium chloride formed is fully dissolved in excess ammonia or in the crude aminosilanes product that is formed under these conditions.

The pressurized and not yet cooled contents of the autoclave are then transferred to another pressure vessel by way of a relief valve (flash process) and at the same time a large portion of the excess ammonia is removed by distillation under pressure with the pressure being regulated at approximately 18 to 20 bar in this evaporation unit.

After complete transposition of the reaction batch from the autoclave to the first evaporation unit, the flash valve is closed and the pressure is relieved gradually in the autoclave by means of water-cooled or –40° C.-cooled condensers and the autoclave is then replenished with the ducts and heated.

The contents of the first evaporation unit are heated to 50° C. to 60° C. by means of a circulatory evaporator and further ammonia is removed by distillation to a residual pressure of approximately 15 bar. After approx. 1 hour around 70% of the excess ammonia is removed from the crude aminosilanes product mixture, without any dissolved ammonium chloride being precipitated from the crude product. The remaining about 60° C. crude aminosilanes product is again transferred to the third process step, the so-called crystallizer, without cooling and under pressure. The flash process is performed in a similar fashion to the first evaporation unit. During the flash process in the crystallizer the residual pressure is regulated to 3 to 5 bar. The flash process in the crystallizer is performed while the crude aminosilanes product/salt mash formed in the container is stirred and heated.

As opposed to the autoclave, there is no further pressure reduction in the empty first evaporator unit, rather, it is replenished with a residual pressure of approx. 12 to 15 bar.

After the entire crude aminosilanes product is transferred to the crystallizer the remaining ammonia is removed by distillation under constant stirring and heating. The internal temperature of the crystallizer is lowered gradually to approx. 1 bar at 20° C. internal temperature. In this process residual ammonium chloride in crystalline form precipitates from the crude aminosilanes product and is held in suspension by the agitation process. The pressure relief in the crystallizer is complete after some 3 to 4 hours. The crude product mash is then withdrawn into a storage vessel and the residual ammonia is pressure-relieved in the waste gas system. The contents of the storage vessel are transferred to a filter dryer, the crude aminosilanes product is separated from the ammonium chloride, the filter cake is washed in the usual manner with a washing fluid, such as toluene, gasoline, hexane or similar fluid, and the filtrates are separated into their individual constituents by means of vacuum distillation.

On completion of distillation 6.05 to 6.4 kg of 3-aminopropyltriethoxy silane is obtained in a purity, determined by gas chromatography, of approximately 98.5 to 99.0 GC-WLDFL % and a chloride content of 20 to 50 ppm.

The yield of 3-aminopropyltriethoxysilane following distillation amounts to about 88% to 92%. The quantities of liquid ammonia or washing fluid recovered during the pressure or vacuum distillation are reused to manufacture 3-aminopropyltriethoxysilane.

Example 2
Manufacture of 3-aminopropyltrimethoxy silane

In a similar fashion to Example 1, 6.2 kg (31.1 mol) 3-chloropropyltrimethoxysilane are reacted with 24 kg (1412 mol) ammonia at 48 to 50 bar and around 100° C. within 6 hours, after which excess ammonia is removed by two flash processes and pressure distillation, as per Example 1. After filtration and cleaning by distillation under vacuum, 4.8 to 5.1 kg of 3-aminopropyltrimethoxysilane are obtained in a purity, determined by gas chromatography, of approximately 98.4 to 99.0 WLDFL % and a chloride content of 20 to 65 ppm. The yield after distillation is 86% to 91%.

Example 3
Manufacture of 3-aminopropylmethyldiethoxysilane

According to Example 1, 6.6 kg (31.1 mol) 3-chloropropylmethyldiethoxysilane are reacted with 24 kg (1412 mol) ammonia, excess ammonia is removed by pressure distillation and flash processes and the 3-aminopropylmethyldiethoxysilane that is formed is isolated by filtration and vacuum distillation.

A 5.4 to 5.5 kg amount of 3-aminopropylmethyldiethoxysilane at a yield of 90% to 93% are obtained in a purity, determined by gas chromatography, of 98.7 to 99.3 GC-WLDFL % and a chloride content of 16 to 45 ppm.

The disclosure of German priority Application Number 10058620.1 dated Nov. 25, 2000 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process for the manufacture of aminoalkylsilanes of formula I:

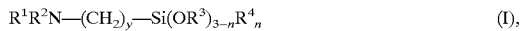

$$R^1R^2N-(CH_2)_y-Si(OR^3)_{3-n}R^4{}_n \quad (I),$$

wherein $R^1$ and $R^2$ are each independently, identical or different, hydrogen, aryl, arylalkyl or $C_{1-4}$-alkyl; $R^3$ and $R^4$ are each independently, identical or different, $C_{1-8}$-alkyl or aryl; y is 2, 3 or 4 and n is 0 or 1, 2 or 3, comprising:

reacting an organosilane of formula II:

$$X-(CH_2)_y-Si(OR^3)_{3-n}R^4{}_n \quad (II),$$

wherein X is Cl, Br, I or F; and $R^3$, $R^4$, y and n are each as defined above with ammonia or an organic amine compound of the formula:

$$HNR^1R^2 \quad (III),$$

wherein $R^1$ and $R^2$ are each as defined above with at least one of $R^1$ and $R^2$ not being hydrogen in a liquid phase;

evaporating ammonia or organic amine under reduced pressure while ammonium chloride or aminohydrochloride by-products, produced in the reaction of the first step, remains dissolved in the liquid phase;

transferring the product mixture after said evaporation to another vessel operated at a lower pressure level of than the second stage, and allowing ammonium chloride or aminohydrochloride to crystallize;

separating the crystalline ammonium chloride or aminohydrochloride from the crude product; and distilling the crude product to produce purified aminoalkylsilane product.

2. The process as claimed in claim 1, wherein the reaction in the first process step occurs at a pressure of 25 to <100 bar abs. and at a temperature ranging from 50 to <110° C.

3. The process as claimed in claim 1, wherein the second evaporative step is performed at a pressure of >10 to <50 bar abs and at a temperature of 10 to <110° C.

4. The process as claimed in claim 3, wherein the second evaporative step is performed at a pressure of 11 to 35 bar abs and at a temperature of 20° C. to 95° C.

5. The process as claimed in claim 2, wherein the second evaporative step is performed at a pressure of 13 to 25 bar abs and at a temperature of 30° C. to 85° C.

6. The process as claimed in claim 3, wherein the average product dwell time in the second evaporative step is adjusted to 0.1 to 4 hours.

7. The process as claimed in claim 1, wherein the third step of crystallization is performed at a pressure below the final pressure of the second evaporative stage.

8. The process as claimed in claim 5, wherein the third process step of crystallization is performed at a pressure of 1 to 6 bar abs.

9. The process as claimed in claim 1, wherein the aminoalkylsilane is a 3-chloralkylalkoxysilane selected from the group consisting of 3-chloropropyltriethoxysilane, 3-chloropropyltrimethoxysilane, 3-chloropropylmethyldimethoxysilane, 3-chloropropylmethyldiethoxysilane, 3-chloropropyldiethylmethoxysilane and 3-chloropropylethylpropylethoxysilane.

10. The process as claimed in claim 1, wherein the organic amine compound is methylamine, ethylamine or diethylamine.

11. The process as claimed in claim 1, wherein the aminoalkylsilane product is a compound selected from the group consisting of 3-aminopropyltriethoxysilane, 3-aminopropyltrimethoxysilane, 3-aminopropylmethyldiethoxysilane and N-methyl-3-aminopropyltrimethoxysilane.

12. The process as claimed in claim 1, wherein the molar ratio of haloralkylalkoxysilane to ammonia or organic amine compound ranges from 1:10 to 1:50.

* * * * *